United States Patent
Kumar (10) Patent No.: US 9,153,900 B2
(45) Date of Patent: Oct. 6, 2015

(54) IMPLANTABLE SUBCUTANEOUS ELECTRICAL SOCKET AND PERCUTANEOUS PLUG

(75) Inventor: Mukesh Kumar, Warsaw, IN (US)

(73) Assignee: BIOMET MANUFACTURING CORP., Warsaw, IN (US)

( * ) Notice: Subject to any disclaimer, the term of this patent is extended or adjusted under 35 U.S.C. 154(b) by 303 days.

(21) Appl. No.: 13/274,300

(22) Filed: Oct. 14, 2011

(65) Prior Publication Data
US 2013/0096602 A1 Apr. 18, 2013

(51) Int. Cl.
| | |
|---|---|
| *A61N 1/372* | (2006.01) |
| *H01R 13/52* | (2006.01) |
| A61N 1/378 | (2006.01) |
| H01R 4/24 | (2006.01) |
| A61B 17/72 | (2006.01) |
| A61B 17/68 | (2006.01) |

(52) U.S. Cl.
CPC ......... *H01R 13/5219* (2013.01); *A61B 17/7216* (2013.01); *A61B 2017/681* (2013.01); *A61N 1/3787* (2013.01); *H01R 4/2445* (2013.01); *H01R 13/5224* (2013.01); *H01R 2201/12* (2013.01)

(58) Field of Classification Search
CPC .......... H01R 13/5219; H01R 13/5224; H01R 2201/12; A61N 1/3787; A61N 1/378; A61N 1/375
USPC .......................................... 607/33; 439/909
See application file for complete search history.

(56) References Cited

U.S. PATENT DOCUMENTS

| | | |
|---|---|---|
| 5,205,286 A | 4/1993 | Soukup et al. |
| 5,701,895 A | 12/1997 | Prutchi et al. |
| 5,782,645 A | 7/1998 | Stobie et al. |
| 5,873,368 A | 2/1999 | Sabin |
| 5,904,646 A | 5/1999 | Jarvik |
| 6,070,103 A * | 5/2000 | Ogden ........................... 607/60 |
| 6,245,075 B1 | 6/2001 | Betz et al. |
| 6,383,185 B1 | 5/2002 | Baumgart |
| 6,916,290 B2 | 7/2005 | Hedengren et al. |

(Continued)

FOREIGN PATENT DOCUMENTS

| | | |
|---|---|---|
| WO | 9222268 A1 | 12/1992 |
| WO | 2009060427 A1 | 5/2009 |
| WO | 2011035308 A1 | 3/2011 |

OTHER PUBLICATIONS

Robinson et al, "Mandibular Distraction Force: Laboratory Data and Clinical Correlation", 2001, J. Oral Maxillofac Surg., 59:539-544.

(Continued)

*Primary Examiner* — Tammie K Heller
(74) *Attorney, Agent, or Firm* — Hahn & Voight PLLC; Roger C. Hahn (57) ABSTRACT

An implantable subcutaneous electrical socket and corresponding percutaneous plug are disclosed for controlling and/or energizing an implanted medical device, such as a bone distraction motor, within a patient. The subcutaneous electrical socket is accessed percutaneously by the plug, to connect data and power electrodes deployed from the plug into the socket to conduct control signals and electrical power from an external source to an implanted medical device within the patient. The socket and plug include insulating materials to prevent electrical shock to the patient.

29 Claims, 6 Drawing Sheets

(56) References Cited

U.S. PATENT DOCUMENTS

| | | |
|---|---|---|
| 7,135,022 B2 | 11/2006 | Kosashvili et al. |
| 7,615,052 B2 | 11/2009 | Serbousek |
| 8,483,820 B2 * | 7/2013 | Zilberman et al. ............... 607/2 |
| 2006/0121415 A1 | 6/2006 | Anitua Aldecoa |
| 2009/0192514 A1 | 7/2009 | Feinberg et al. |
| 2009/0259319 A1 | 10/2009 | DiSilvestro et al. |
| 2010/0121323 A1 | 5/2010 | Pool et al. |
| 2010/0222677 A1 | 9/2010 | Placek et al. |
| 2010/0249644 A1 | 9/2010 | Miles et al. |
| 2010/0262158 A1 | 10/2010 | Siegel et al. |
| 2010/0262239 A1 | 10/2010 | Boyden et al. |
| 2010/0262247 A1 | 10/2010 | Arnin |
| 2011/0106071 A1 | 5/2011 | Bosel |
| 2013/0204316 A1 * | 8/2013 | Carpentier et al. ............. 607/45 |

OTHER PUBLICATIONS

Kim et al, "Fabrication and analysis of plastic hypodermic needles", Jul./Aug. 2005, Journal of Medical Engineering & Technology, vol. 29, No. 4, pp. 181-186.

* cited by examiner

IMPLANTABLE SUBCUTANEOUS ELECTRICAL SOCKET AND PERCUTANEOUS PLUG

FIELD OF THE INVENTION

This disclosure relates to systems and methods for delivering electrical power to a medical device implanted in a subject. The systems and methods employ a non-implantable plug having a retractable needle, and an electrical socket implanted below the skin of the subject. The retractable needle structure is capable of piercing the skin of the subject to contact the electrical socket. The retractable needle structure includes an outer hollow needle containing a non-conductive material and an inner electrode capable of conducting electricity or data. The electrodes are moveable from a non-deployed, or retracted, position completely within the hollow needle and a deployed position where the electrode makes an electrical contact with a conductive material within the implanted electrical socket.

BACKGROUND

Several types of implantable medical devices require electricity to operate. Implantable medical devices such as distraction or adjustment devices can be implanted in subjects to correct structural malformations or injuries to the skeletal and muscular system. Many different types of distraction devices are known. For examples, devices are known in the art for the correction of spinal sclerosis, stenosis and other spinal conditions (e.g. U.S. Pat. No. 7,615,052, U.S. 2010/0262247), for lengthening long bones of the arm or legs (e.g. U.S. Pat. Nos. 6,245,075, 6,383,185), treatment of micrognathia, and for craniofacial correction (e.g. U.S. 2009/0192514). Many apparatus design elements are known for the manufacture of distraction devices including devices designed for promoting osteogenesis over an extended time period of treatment.

Due to the slow growth rate of osseous tissue, distraction devices typically operate through the application of small changes in force over time to correct bone structure. For example, a distraction device can have two or more attachment points for connecting to bone in a subject and a distraction or adjustment mechanism to adjust a distance between the two attachment points over time. In a typical treatment, each adjustment of the distraction device can be 5 mm or less in distance due to the slow growth rate of osseous tissue. Numerous adjustments are made to the distraction device, sometimes over several months, with the distraction device implanted below the dermis and often the musculature of the subject.

Early distraction devices contained a frame or other scaffolding located outside of the subject's tissues with one or more pins extending through the subject's skin and connected to the bone or a separate distraction device. Adjustments to the frame were made periodically to affect adjustment of the distraction device. Hence, the implanted distraction device was adjustable over the extended time course of treatment despite the location of actual attachment to the bone being located under the skin and musculature. However, the external frame of the device is often heavy and cumbersome to the patient. Further, the pins or other transcutaneous elements extending from the external environment into the tissue of the patient are a source for infection and scarring.

Mandibular distraction is a treatment for the correction of micrognathia, and such treatment is frequently utilized for micrognathism in children. With children in particular, there are issues associated with current distraction solutions. The expansion of mandibular distraction devices is generally actuated via an input of mechanical force by an operator, typically a parent, however there remains the possibility of the child actuating the mechanism themselves, accidental or otherwise. Additionally, there are emotional aspects associated with the unaesthetic appearance of mandibular distraction devices protruding from the skin. A completely implanted device would be particularly useful for addressing these concerns, primarily in children, and to a lesser extent in adults. However, an implanted solution presents the problem of transmitting the energy necessary to actuate the device.

To avoid the complications caused by an external frame, systems where the entire device is implanted into the patient have been developed. In some instances, the device has a mechanical action that can be activated through external manipulation of the subject; however, operation of such devices is difficult. Other devices require the subject to be sedated for surgery and an incision made to gain access to the implanted device for the purpose of manual adjustment of the implant. The subject is undesirably subjected to risk of infection and complications from sedation.

Completely implantable devices without transcutaneous elements require a source of power other than direct mechanical power provided by a medical professional performing an adjustment. More recent devices include the implantation of a motor and power source, such as a battery, into the patient. For example, WO 92/22268 teaches a device where a motor, battery, and pre-programmed control components are implanted, where the control components carry out a preset series of instructions to adjust the distraction device. However, the course of treatment cannot be modified after the device is implanted. To overcome this limitation, other devices have been developed that contain an RF receiver to receive instructions from an external controller, for example, US 2009/0192514. However, such systems require capacitors and other electrical components to be implanted within a patient, with the capacitors serving as the sole power source over an extended course of treatment. The quality and duration of treatment deliverable by such systems is limited by the implanted power source. Further, there are risks inherent to implanting energized electrical components within a patient. Additionally, RF control signals can be obstructed in the cases of obese patients.

Some systems have addressed the limitation of the amount of total power capacity of an implantable battery through the use of a rechargeable battery or a motor operable by a current induced from an applied magnetic field (e.g. U.S. Pat. No. 7,135,022, U.S. 2010/0262247). The amount of energy that can be practically delivered by induction is limited. Further, batteries suitable for implantation are limited in their rate of current discharge even if rechargeable. Hence, the amount of mechanical work that can be performed to affect the adjustment is limited. Further, batteries and capacitors contain toxic materials that represent an elevated risk when implanted into the patient.

Systems which directly connect an electrical source to an implanted medical device conduct electricity at low voltages and currents but are generally restricted to data transmission to and from the medical device. The capacity for electrical transmission of such systems is unsuitable for operation of medical devices having high electrical operating requirements.

Due to the limitations discussed above, the scope of implanted medical devices requiring electricity is restricted to data transmission to and from devices, which require only small operating voltages and currents. Additionally, the types of therapies deliverable to a patient by an electrically operated implanted medical device is similarly limited due to the low power transmission capacities of induction and/or battery operated systems. Therapies and devices which might require a comparably higher degree of electrical transmission to an implanted device for treatment undesirably pose risks of electrical shock to both patients and operators.

Still other devices have contemplated the use of a magnetic field to affect adjustment of an implanted distraction device by interaction with magnetic components included with the implanted part of the device (e.g. U.S. 2009/0192514, U.S. 2010/0262239, WO 2009/060427, WO 2011/035308). However, the amount of torque force that can be developed by manipulation of an external magnetic field is often limited in practice leading to a similar limitation compared to devices including an implanted battery. As such, there is a need for a system that can deliver a higher voltage and current to implanted devices than currently available systems, without posing the risk of electric shock to patients and operators.

SUMMARY OF THE INVENTION

The invention is directed to a medical device for establishing percutaneous delivery of electrical current to a separate implanted medical device within a subject including a percutaneous electrical plug having at least two electrodes for conducting electricity from a connected power source into an implantable subcutaneous electrical socket which receives the plug. Each electrode is located within a hollow needle that protrudes from the plug and is movable between a non-deployed position, wherein the electrodes are concealed within the hollow needles, and a deployed position, wherein tips of the electrodes protrude from the hollow needles. The hollow needles are movable between a retracted position where the hollow needles do not extend from the skin contact surface and a percutaneous position where the hollow needles extend from the skin contact surface wherein each power electrode can be deployed independent of the position of the hollow needles. The implantable subcutaneous electrical socket includes receiving ports for the hollow needles, wherein the receiving ports are electrically insulated from each other, and each have a conductive base material located at the bottom. The hollow needles of the percutaneous plug pierce the subject's skin and enter the receiving ports of the implantable subcutaneous electrical socket, thereafter deploying the electrode tips to contact the conductive base material of the receiving ports and complete an electrical connection between the plug and the electrical socket. A power source is connected to the plug via electrical wires and supplies an electrical current and voltage which is conveyed into the implantable subcutaneous electrical socket. A separate implanted medical device within the subject is connected to the implantable subcutaneous electrical socket via electrical wires and receives the electrical current and voltage supplied by the power source. Other embodiments include data electrodes that convey data signals between a separate implanted medical device and a controller. In any embodiment of the invention, the subject is insulated from the electricity conveyed through the percutaneous plug and implantable subcutaneous electrical socket.

A method is contemplated for conveying electricity to a separate implanted medical device within a subject having the steps of subcutaneously implanting a subcutaneous electrical socket according to the invention within a subject, connecting a percutaneous plug to the electrical socket through the skin of the subject wherein electrodes of the plug are in a non-deployed position within hollow needles protruding from the plug, and deploying the electrodes into receiving ports within the implantable subcutaneous electrical socket to establish an electrical connection with a conductive base material of the ports.

An embodiment is contemplated wherein the percutaneous plug and implantable subcutaneous electrical socket of the invention supply electricity from a power source to a bone distraction device implanted within the bone tissue of a subject that includes a first and second attachment point, a distraction mechanism, and an electric motor for varying the distance between the first and second attachment points. The distance between the first and second attachment points of the bone distraction device is adjusted by operating the motor of the distraction device via the percutaneous plug and implantable subcutaneous electrical socket.

DETAILED DESCRIPTION OF THE INVENTION

The present invention includes a subcutaneously implantable electrical socket and an electrical plug that percutaneously interfaces with the implantable socket. The implantable subcutaneous electrical socket and percutaneous plug connect a separate implanted medical device such as a distraction motor to an external electrical source and control device where the plug and socket are used to convey electricity to the electric motor and/or to establish electrical communication between the implanted medical device and a control device. In certain embodiments, the implantable subcutaneous electrical socket is suitable for delivering electricity to a motor-driven expandable medical device implanted within a patient for bone distraction operations, with the degree of bone distraction controlled by an external device having a separate or integrated power supply, and in electrical communication with the implanted medical device.

In operation, the subcutaneous electrical socket is implanted in a patient, below the skin, and is accessed percutaneously by an electric plug having a plurality of hollow needles. The electrical socket is implanted at a depth which facilitates easy access by the percutaneous plug and limits the amount of pain experienced by the patient to the extent possible. The body of the implantable subcutaneous electrical socket is constructed of a rigid biocompatible material that is electrically insulating and includes a plurality of receiving ports. The hollow needles extend from a skin contacting surface of the percutaneous plug and facilitate connection of the plug to the socket by piercing the patient's skin. The percutaneous plug is placed on the region of a patient's skin located above the implanted subcutaneous electrical socket. The plug and socket are aligned by a complimentary shaping of the plug and socket, the features of the socket being palpable through the patient's skin. After piercing the patient's skin, the hollow needles of the electric plug mate with the receiving ports within the implantable subcutaneous electrical socket wherein the plurality of hollow needles includes at least two hollow needles which deploy power electrodes. In certain embodiments, additional hollow needles can deploy data electrodes. In other embodiments, the electric plug includes data electrodes having a non-insulated needle tip that do not require the use of insulating hollow needles. The receiving ports of the implantable subcutaneous electrical socket in some configurations can be filled and/or capped with an electrically insulating self sealing material that is penetrable by the hollow needles and electrodes. Other configurations may rely on insulating coating or materials known in the art and still others may only require the electrode retracted to a sufficient depth within the hollow needle to prevent accidental electrical contact. Once the hollow needles of the plug are mated with the receiving ports of the implantable subcutaneous electrical socket, the hollow needles carrying a power electrode deploy the electrode through the self sealing material of the receiving ports to establish electrical contact with a conductive base material located at the bottom of the receiving ports. Embodiments are contemplated in which no insulating material is contained in the hollow needle or in which the hollow needle is coated with an insulating material. In embodiments that include hollow needles with deployable data electrodes, the data electrodes can be deployed through the self sealing material of the receiving ports to establish electrical contact with a conductive base material at the bottom of the receiving ports. Where the data electrodes have a needle tip, the data electrodes can percutaneously access the receiving ports similar to the hollow needles where the data electrodes carry a low electrical current suitable for data transmission but at a level insufficient to cause harm to the patient. In general, the power electrodes will carry an operating electrical current and voltage suitable to drive an implantable motor and related electrical components as contemplated by the invention and are thus, desirably electrically insulated from the hollow needles.

In other embodiments, the percutaneous plug conceals hollow needles which are deployable from a retracted position within the plug to a percutaneous position extending from the contact surface of the plug. From the percutaneous position, the hollow needles deploy power electrodes and data electrodes disposed therein. Once the plug and socket are aligned, the hollow needles are deployed from the retracted position to the percutaneous position, piercing the patient's skin as they are inserted into the receiving ports of the electrical socket. Once the hollow needles are in place within the receiving ports of the electrical socket, power and data electrodes are deployed from the hollow needles to contact the conductive base material located at the bottom of the receiving ports.

Definitions

The articles "a" and "an" are used herein to refer to one or to more than one (i.e., to at least one) of the grammatical object of the article. By way of example, "an element" means one element or more than one element.

The term "antimicrobial" refers to a property of inhibiting growth of microorganisms.

The term "biocompatible" refers to a material that can be accepted upon implantation into a body that does not irritate surrounding tissues. The biocompatible material should not provoke an inflammatory response or allergic reactions.

A "catheter" is a tube or duct that is implantable within the body of a patient for directing materials disposed therein from one location to another.

The term "comprising" includes, but is not limited to, whatever follows the word "comprising." Thus, use of the term indicates that the listed elements are required or mandatory but that other elements are optional and may or may not be present.

The term "consisting essentially of" includes whatever follows the term "consisting essentially of" and additional elements, structures, acts or features that do not affect the basic operation of the apparatus, structure or method described.

The term "consisting of" includes and is limited to whatever follows the phrase "consisting of." Thus, the phrase indicates that the limited elements are required or mandatory and that no other elements may be present.

A "controller," "control unit," "processor," or "microprocessor" is a device which monitors and affects the operational conditions of a given system including the amount of current or electrical potential supplied by a electrical power source. The operational conditions are typically referred to as output variables of the system, which can be affected by adjusting certain input variables.

The term "data electrode" refers to a structure made from a conductive material having sufficient structure to pass a current or communicate a voltage difference that can encode data or information.

The term "distraction device" or "bone distraction device" refers to a device used to perform distraction osteogenesis or correct injuries, defects or abnormalities of osseous tissue by directing the growth of new osseous tissue. A distraction device can operate by application of a force to osseous tissue that is modified over a time course of treatment.

The term "electric motor" refers to any device that can generate mechanical energy from an electric current or potential applied to the device.

The term "electrical contact" refers to two objects that come into direct contact or separated by a material that has a dielectric constant less than the dielectric constant for a vacuum such that a flow of electric current between the two objects is facilitated.

The term "electrical power source" refers to any source of stored or generated electrical current or potential, which can be an AC or a DC current, including batteries, electrical generators, an electrical rectifier, an electrical inverter or an electrical transformer.

As used herein, "electrically conductive" material refers to a material through which readily allows current flows at the voltages typically applied to the electrodes of the present invention. Non-limiting examples of electrically conductive material include metallic conductors, conductive polymers, and semi-conductors with appreciable conductivity.

The term "electrically insulated" refers to two objects separated by a material that has a dielectric constant greater than the dielectric constant for a vacuum such that a flow of electric current between the two objects is resisted.

As used herein, "electrically non-conductive" material refers to a material that allows no current or little current to flow at the voltages typically applied to the electrically conductive components of the invention. Non-limiting examples of electrically non-conductive materials include insulators such as plastics and other non-conductive polymers, non-conductive inorganics such as oxides, and semi-conductors exhibiting low conductivity such as un-doped silicon.

The term "electrical plug" refers to a structure delivering and/or passing an electrical current to another component or structure.

The term "hermetically sealed" refers to a state of being sealed against the entrance of solids, liquids, and gases.

The term "hollow needle" refers to a structure having a piercing end with sufficient sharpness to penetrate skin, including human skin, in a fashion such that the disruption to the skin is not of a dimension substantially larger than the hollow needle; the hollow needle has an internal space than can accommodate another object including a power electrode or a data electrode as defined herein.

The term "implantable" is used to describe medical devices that are capable of being implanted within the body of a patient for a substantial period of time. Device implantation is accomplished via a surgical procedure or other suitable medical procedure.

The term "implantable subcutaneous electrical socket" refers to a structure that can receive an electrical current from another component or structure and prevent the leakage of the current being received to surrounding body tissues of a subject in which the implantable subcutaneous electrical socket is implanted.

The term "insulation material" or "insulator" refers to a material having a dielectric constant greater than the dielectric constant of a vacuum.

The term "medical device" refers to any device requiring the use of electricity to perform a therapeutic function.

The terms "patient" or "subject" refer to a recipient of medical treatment.

The term "percutaneous" refers to the state of traversing the skin of a patient or going through skin by piercing or other means.

The term "power electrode" refers to a structure made from a conductive material having sufficient structure to pass an operational electric current of at least 0.01 A at a potential of at least 0.05 V.

The terms "re-sealable" and "self sealing" as they relate to an insulation material refer to a material that is penetrable by an object, such as needle or hollow needle, and is capable of refilling the space occupied by the penetrating object after the penetrating object is removed.

The term "skin" includes the epidermal and dermal layers of external tissue of a mammalian body, particularly humans.

The terms "solid conductor" and "wire" refer to an electrically conductive material for carrying electricity from one object to another.

The term "subcutaneous" refers to the region below the dermal layer of skin of a mammalian body, particularly humans.

Implantable Subcutaneous Electrical Socket and Percutaneous Plug

Figure 1:
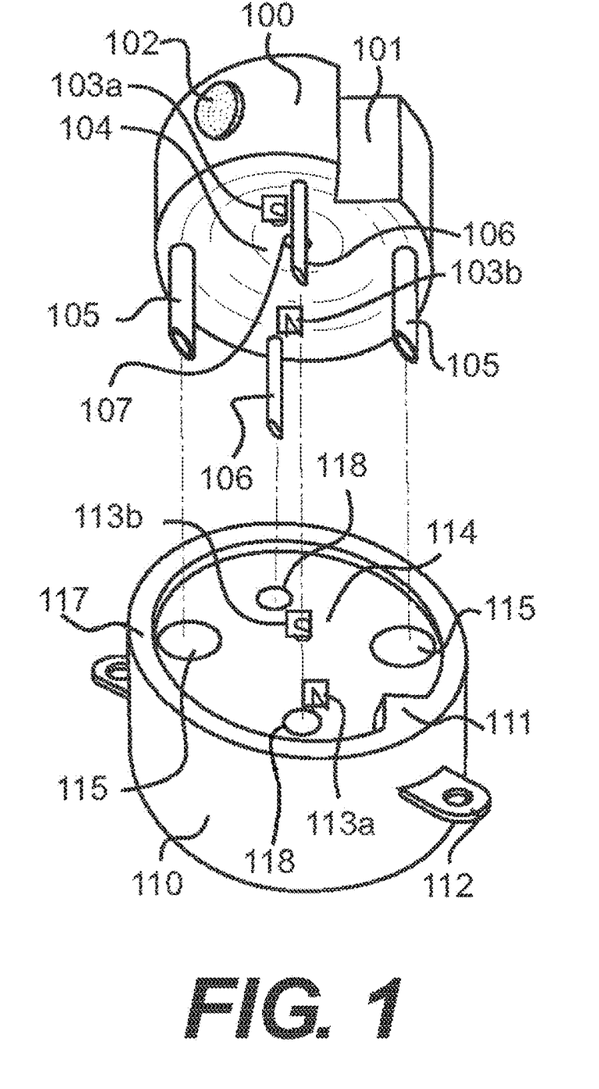
FIG. 1 shows a perspective view of an embodiment of an implantable subcutaneous electrical socket and percutaneous plug according to the present invention.
Figure 2:
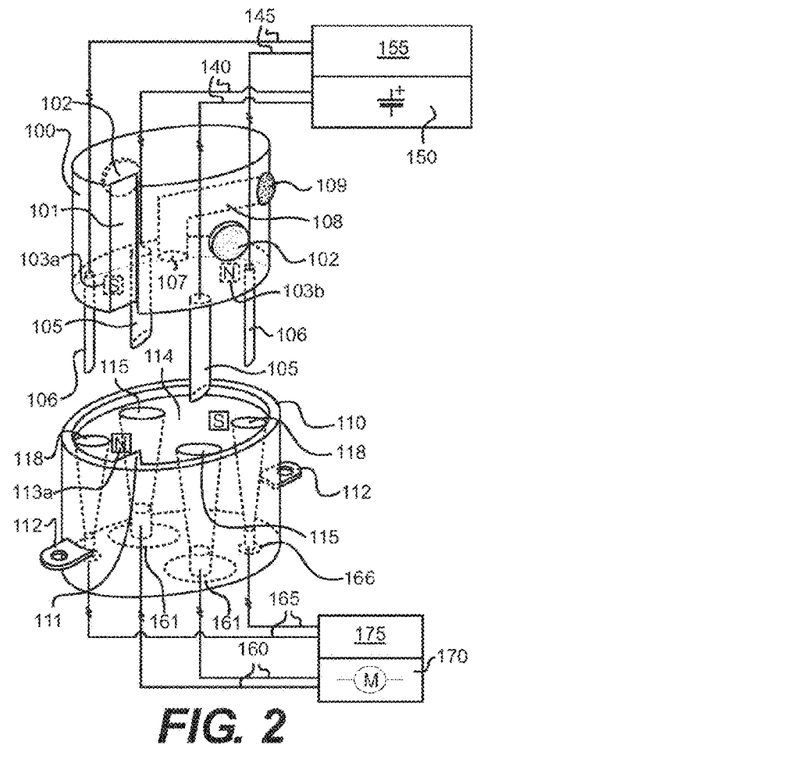
FIG. 2 shows a perspective view of the embodiment of FIG. 1 wherein the percutaneous plug is connected to an external control device and power source, and the implantable subcutaneous electrical socket is connected to a medical device and motor.

Referring to FIGS. 1 and 2, an implantable subcutaneous electrical socket socket 110 and a plug 100 of the electrical socket system are shown. The implantable subcutaneous electrical socket 110 is implanted in a patient subcutaneously and affixed in place by any known means such as suturing holes 112, near the location of an implanted medical device 175 to be energized. Suitable locations for subcutaneous electrical socket implantation within a patient include the thigh, forearm, and mandibular jaw line, however one skilled in the art will recognize that other socket implant locations may be contemplated, depending on, for example, patient anatomy and the location and type of the implanted medical device to be energized. The distance from the implantable subcutaneous electrical socket 110 to the implanted medical device should be determined such that the length of internal electrical wires 160 and 165 to convey data and electricity from the socket to the implanted medical device 175 is minimized to reduce the risk of signal and data loss. In one embodiment, the internal electrical wires 160, 165 are embedded within the electrically insulating material of the implantable subcutaneous electrical socket 110 and extend therefrom in a protective catheter constructed of an electrically insulating biocompatible material before connecting to an implanted medical device. In another embodiment, the electrical wires 160, 165 are encased in an electrically insulating biocompatible material to isolate the wires and conducted electricity from the patient. Electrically insulating biocompatible materials can include polytetrafluoroethylene, polyethylene terepthalate, polytetrafluoroethylene, polyurethane, polyvinyl chloride, silicone, or any suitable material known to those of ordinary skill that complies with ISO 10993.

The implantable subcutaneous electrical socket 110 has a plurality of receiving ports 115, 118 arranged across a top surface 114 of the socket 110. In the embodiment shown in FIGS. 1 and 2, hollow needles 105 and data electrodes 106 protrude from a skin surface side 104 of the plug 100. Referring to FIGS. 1 and 2, the receiving ports 115 receive hollow needles 105, and the receiving ports 118 receive data electrodes 106.

Figure 3A:
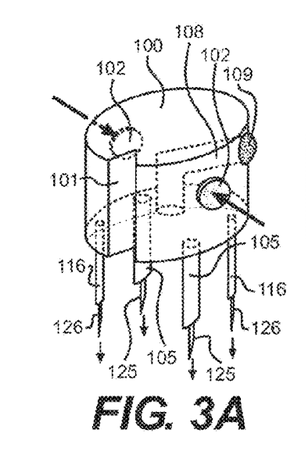
FIGS. 3A-3C show perspective views of an embodiment of a percutaneous plug according to the present invention illustrating actuation of deployable electrodes.
Figure 3B:
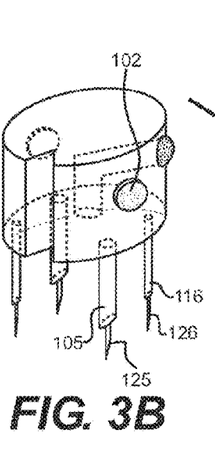
Figure 3C:
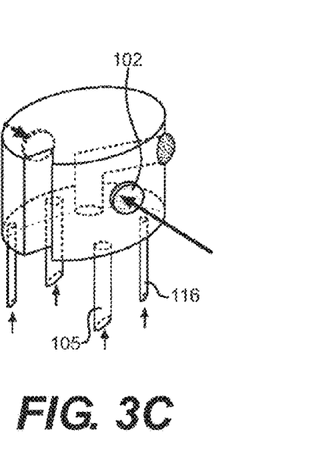
Figure 4A:
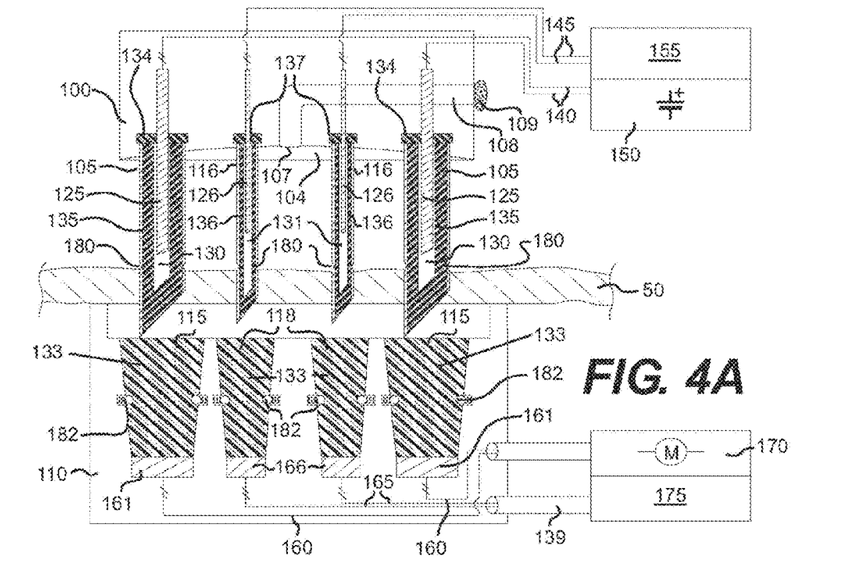
FIGS. 4A and 4B show cut-away side views of embodiments of implantable subcutaneous electrical sockets and percutaneous plugs according to the present invention.
Figure 4B:
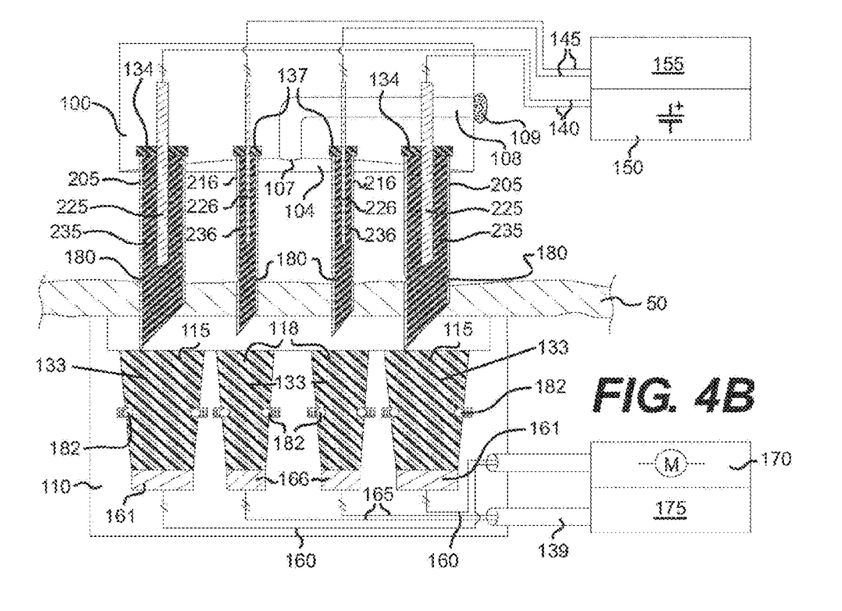

FIGS. 3 and 4 show embodiments having deployable data electrodes in addition to deployable power electrodes. Referring to FIG. 4A, hollow needles 105 and hollow needles 116 protrude from the skin surface side 104 of the plug 100, with power electrodes 125 deployable from hollow needles 105 and data electrodes 126 deployable from hollow needles 116.

In any embodiment, receiving ports 115, 118 are sized differently to accommodate the size of the corresponding hollow needles 105, 116 and/or data electrodes 106. The receiving ports 115, 118 are arranged along a surface 114 of the socket 110 such that interface of the plug 100 with the socket 110 is restricted to a proper alignment. As shown in FIG. 1, the surface 114 of the socket 110 may include a lip 117 to assist in such alignment.

In any embodiment, the power electrodes 125 conduct electricity at an operating current or voltage. In the embodiment shown in FIGS. 1 and 2, the data electrodes 106 are fixed in a position that protrudes from the plug 100. When the plug 100 is inserted into the port 110, the data electrodes 106 pierce the skin of the patient, similar to the hollow needles 105, and enter the receiving ports 118. In certain embodiments, the data electrodes are suitable only for carrying the small voltages and currents associated with data transmission, and thus do not require the protective measures of the power electrodes to reduce the risk of electric shock to the patient and operator when conducting electricity. In the embodiment shown in FIGS. 3 and 4, the hollow needles 116 include deployable data electrodes 126 similar to the hollow needles 105 containing deployable power electrodes 125. In other embodiments, the power electrodes 125 can be larger than the data electrodes 106, 116 due to the difference in the magnitude of the electrical current and voltage conducted by each.

Accordingly, the implantable subcutaneous electrical socket and percutaneous plug systems of the present invention allow for connection of an external power source and/or device to a motorized medical device implanted within a patient, with separate electrical connections for operating current/voltage and data transmission.

As shown in FIG. 1, the implantable subcutaneous electrical socket 110 includes a tooth 111 which fits into a corresponding notch 101 on the plug 100 that is geometrically complimentary to the tooth 111. The tooth 111 can be perceptible through a patient's skin via touch or sight to assist in the location of the implantable subcutaneous electrical socket 110, and to facilitate proper alignment of the plug 100 as it is connected to the socket. The invention is not limited to the tooth and notch arrangement and any alternative complementary means for facilitating the alignment of the plug to the socket is contemplated. For example, the surface 114 of the socket 110 can be concave and the surface 104 of the plug 100 convex (not shown). Alternatively, the surface 114 of the socket 110 can be convex to produce a bulge visible upon implantation and the surface 104 of the plug 100 can be concave to accommodate such bulge when mating the plug 100 to the socket 110. The shape of the plug 100 and socket 110 can be of any suitable symmetry, geometry, size or shape to facilitate alignment. It is understood that many alignment configurations of the plug 100 and socket 110 can be envisioned without departing from the invention. The size and arrangement of the hollow needles 105, 116 and/or data electrodes 106 with respect to the matching receiving ports 115, 118 also act to limit the interface of the plug 100 and the implantable subcutaneous electrical socket 110, so as to ensure proper alignment and connection of the plug 100 to the socket 110.

As shown in FIGS. 1-3, the plug 100 and implantable subcutaneous electrical socket 110 are shown in a non-limiting oval configuration shaped to match each other to ensure proper alignment. As shown in FIGS. 1-4, the surface 104 of the plug 100 from which the hollow needles 105, 116 and/or data electrodes 106 protrude is concave and forms a space between the plug 100 and a patient's skin so that air in the space can be evacuated through an airway 108 by a diaphragm 109 to establish a vacuum seal to inhibit movement of the plug while connected to the implantable subcutaneous electrical socket 110. The vacuum operation employing a concave surface is separate from the concave/convex configuration used for alignment purposes. However, a concave surface can be used for either alignment or inhibiting movement or both. In operation, the diaphragm 109 is depressed, pushing the air in airway 108 out through a hole 107, prior to mating the plug 100 with the implanted socket 110. After the plug 100 is in place on a patient's skin, the diaphragm 109 is released, forming a vacuum in airway 108, and sealing the plug 100 to the patient's skin. Any means of achieving vacuum including use of suction cups and vacuum sealing means known to those of ordinary skill are contemplated by the invention. Tape may also be applied to the plug 100 while connected to the electrical socket 110 to further inhibit movement of the plug. Additionally, as shown in FIGS. 1 and 2, of magnets 103a and 103b disposed on the plug 100, matched to magnets 113a and 113b disposed on the implantable subcutaneous electrical socket 110 provide additional nonpermanent fastening of the plug and implantable electrical socket while connected. Many other means for inhibiting movement of the plug can be contemplated without departing from the invention. Further, it will be understood that the proportions reflected in the drawings are non-limiting wherein different relative proportions of the needles, actuation buttons, sockets, plugs and other components of the invention can be configured by one of ordinary skill as appropriate for practical usage.

Referring to FIG. 4, side view schematics of embodiments of the electrical socket and percutaneous plug system having deployable power and data electrodes are shown. In FIG. 4A the hollow needles 105, 116 are shown puncturing a patient's skin in the process of connecting the plug 100 to the implantable subcutaneous electrical socket 110. Each of the hollow needles 105, 116 as shown include a means for securing the hollow needles 105, 116 within the plurality of receiving ports, wherein the means can regulate an amount of penetration of the plurality of hollow needles into the plurality of receiving ports. Such means can include optional locking grooves 180 which interface with optional ball bearing spring locks 182 located within the receiving ports 115, 118. The ball bearing spring locks 182 assist in ensuring the proper insertion depth of the hollow needles 105, 116, and can also lock the hollow needles 105, 116 into place to prevent unintended removal and/or loosening of the plug 100 while engaged with the implantable subcutaneous electrical socket 110. Power electrodes 125 are shown in a non-deployed state within the hollow needles 105. Similarly, data electrodes 126 are shown in a non-deployed state within the hollow needles 116. An insulating cap 134 on top and an interior space 130 within each of the hollow needles 105 insulates the power electrodes 125 from the hollow needles 105 and guides the power electrodes 125 through the hollow needles 105, into the base of the receiving ports 115. Similarly, an insulating cap 137 on top and an interior space 131 within each of the hollow needles 116 insulates the data electrodes 126 from the hollow needles 116 and guides the data electrodes 126 through the hollow needles 116, into the base of receiving ports 118. Insulating material 135, 136 disposed within the hollow needles 105, 116 can be a self-sealing type silicone or other suitable material to insulate the powers electrodes 125 or data electrodes 126 from the hollow needle 105, 116, respectively, in FIG. 4A. Similarly, insulating material 235, 236 in FIG. 4B disposed within the hollow needles 205, 216 can be a self-sealing type silicone or other suitable material to insulate the powers electrodes 225 or data electrodes 226 from the hollow needles 205, 216, respectively.

FIG. 4B shows an embodiment having deployable power electrodes 225 and deployable data electrodes 226 in a non-deployed state within hollow needles 205, 216 that are completely filled with self sealing and electrically insulating material 235, 236 penetrable by the electrodes 225, 226. In certain embodiments, the presence of the self sealing material is optional, for example where the hollow needles 205, 216 are coated in the interior with an insulating material (not shown). In a bloody environment, use of the insulating material can be desirable. The electrodes can be shaped as a needle or without a sharpened or beveled end. The electrodes in any configuration can traverse a sealing material 133 to contact conductive base materials 161, 166.

As shown in FIGS. 4A and 4B, external wires 140 are connected to the power electrodes 125, 225, and connect the electrodes 125, 225 to an external power source 150. External wires 145 are shown connected to the data electrodes 126, 226, and connect the electrodes 126, 226 to an external device 155. The external device 155 may incorporate a power source and a controller, with external wires 140 connected to the power source, and external wires 145 connected to the controller. In another embodiment, the power source and controller may be separate units.

In any embodiment, the receiving ports 115, 118 within the implantable subcutaneous electrical socket can be optionally filled with a re-sealable and electrically insulating material. In certain embodiments, a re-sealable material may not be required. However, in a bloody environment, the re-sealable and electrically insulating material is desirable. An antimicrobial layer (not shown) abutting the skin may be disposed on top of the self-sealing material 133 to prevent infection. The layer can be loaded with any antibiotic suitable for use in a human, including but not limited to erythromycin, clindamycin, azithromycin, clarithromycin, ofloxacin, lomefloxacin, norfloxacin, sulfamethoxazole, vancomycin, ciprofloxacin, tosufloxacin, clinafloxacin, sulbactam, clavulanic acid, and fluconazole. Alternatively, the antimicrobial layer may be present without a self-sealing material or antimicrobial layer. Referring to FIGS. 4A and 4B, each of the receiving ports 115, 118 are packed with an optional sealing material 133 that is re-sealable and electrically insulating. The sealing material 133 is penetrable by the hollow needles 105, 205, 116, 216 and the power electrodes 125, 225, 126, 226 such that the hollow needles and electrodes may be inserted into the receiving ports 115, 118, without damaging the sealing material 133. When the hollow needles 105, 205, 116, 216 and the power electrodes 125, 225, 126, 226 are removed from the receiving ports 115, 118, the sealing material 133 seals the receiving ports to block the entrance of debris and biological materials from the patient. The sealing material 133 may be comprised of an electrically insulating silicone material for re-sealable percutaneous access or any other suitable material known in the art.

Referring to FIG. 4A, conductive base materials 161, 166 are each located at the base of the receiving ports 115, 118 and contact electrodes 125, 126, when deployed, to complete an electrical connection between an external device 155, and power source 150, with an implanted medical device 175 having a motor 170. Internal wires 160 are shown connected to the conductive bases material 161, and are suitable for carrying electrical power at an operating current and voltage to the motor 170 of the implanted medical device 175 when the power electrodes 125, connected to an external power source 150 via external wires 140, are deployed and in contact with the conductive base material 161. Similarly, internal wires 165 are shown connected to the conductive base material 166, and are suitable for conducting data and control signals between the implanted medical device 175 and the external device 155 when the data electrodes 126, connected to the external device 155 via external wires 145, are deployed and in contact with the conductive base material 166. A catheter 139 isolates the segments of the internal wires 160, 165 extending from the implanted electrical socket 110 from surrounding biological tissue in the patient. The catheter 139 is constructed of a flexible, electrically insulating, biocompatible material such as silicone, polytetrafluoroethylene, polyethylene terepthalate, polytetrafluoroethylene, polyurethane, polyvinyl chloride, or any suitable material known to those of skill in the art including those that comply with ISO 10993.

In any embodiment, points of contact between the implantable subcutaneous electrical socket and the surrounding biological matter and tissue of the patient are comprised of an electrically insulated material. The points of contact between the percutaneous plug and the skin of the patient are also comprised of an electrically insulated material. It is primary feature of the invention that no material which conducts electricity within the implantable subcutaneous electrical socket and percutaneous plug makes contact with the patient's skin or tissue. One skilled in the art will recognize that the operation of sockets and plugs of the present invention are such that harmful electrical exposure to the operator and patient is minimized if not eliminated.

Figure 5A:
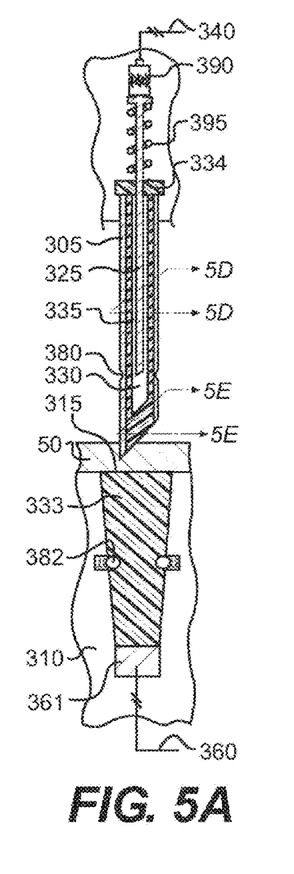
FIGS. 5A-5C show a cut-away side view of a hollow needle of a percutaneous plug according to the present invention and a receiving port of an implantable subcutaneous electrical socket according to the present invention, and illustrate the deployment of an electrode from the hollow needle that is inserted into the receiving port.
Figure 5B:
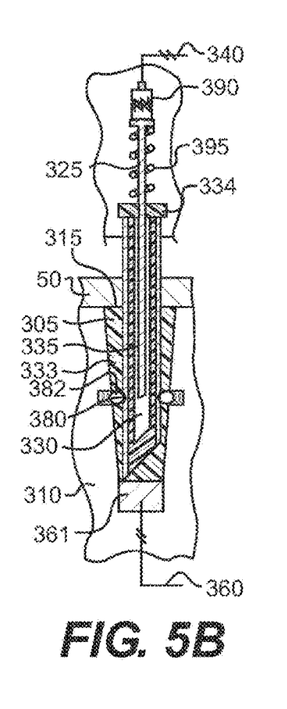
Figure 5C:
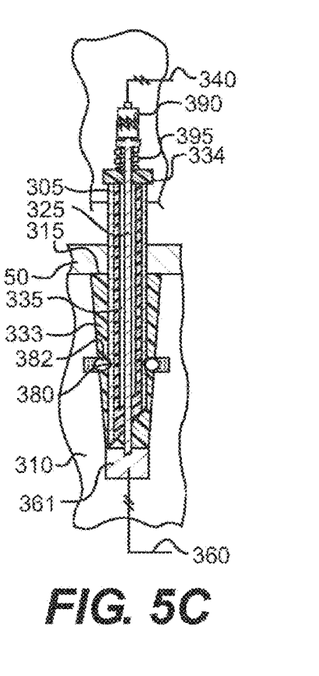

Referring to FIGS. 5A-5C, the figures show a progression of the deployment of an electrode from a hollow needle according to embodiments of the invention. As shown, a hollow needle 305 is inserted through a patient's skin 50, into a receiving port 315, the receiving port 315 being disposed in the implantable subcutaneous electrical socket 310, and an electrode 325 connected to an external wire 340 is subsequently deployed into the receiving port 315 to establish contact with a conductive base material 361 connected to an internal wire 360. The hollow needle 305 includes an insulating cap 334 on top and an insulating liner 335 within the interior space 330 that electrically insulates the hollow needle 305 from the electrode 325. The body of the electrode 325 extending from the top of the hollow needle 305 is encased in electrically insulating material. In some embodiments, the entire length of the electrode 325 is circumferentially encased in insulation, with only the tip exposed.

The piercing end of each the hollow needle 305 includes a re-sealable material which isolates the electrode 325 and interior space 330 from debris and biological material as the hollow needle 305 is inserted through the skin 50. The re-sealable tip is penetrable by the electrode 325 such that when the electrode is deployed, it penetrates the tip as shown in FIG. 5C, and contacts the conductive base material 361 without damaging the tip. When the electrode 325 is retracted, the tip material re-seals the hollow needle 305 to block the entrance of debris and biological materials into the interior space 330 of the hollow needle 305. The re-sealable tip material may be a silicone material or other suitable electrically insulating material known to those skilled in the art. As described above, certain embodiments contemplate hollow needles having interior volumes that are filled with a non-conductive re-sealable material, as shown in FIG. 4B.

As shown in FIG. 5C, once deployed, the electrode 325 contacts the conductive base material 361 located at the bottom of the receiving port 315. The contact of the electrode 325 with the conductive base material 361 completes an electrical connection between the external wire 340 of the plug and the internal wire 360 of the electrical socket. The contact establishes an electrical connection between an implanted medical device and an external device and/or power supply. In some embodiments, a portion of the electrode 325 may pass through insulating material 333.

In the embodiment shown in FIGS. 2, and 4A, one pair of receiving ports 115 within the implantable subcutaneous electrical socket 110 act as a positive and negative electrical lead pair and facilitates connection of the power electrodes 125 to the conductive base material 161 at the bottom of the receiving ports 115 for conducting an operating electrical current and voltage to an implanted medical device 175 from an external power source 150. Another pair of receiving ports 118 facilitates connection to the conductive base material 166 for conducting data and control signals between the implanted medical device 175 and an external device 155.

Engagement of an optional locking and insertion depth regulation mechanism is shown in FIGS. 4 and 5A-5C. Once the hollow needles 105, 205, 305 are inserted into the receiving ports 115, 315, locking grooves 180, 380 interface with ball bearing spring locks 182, 382 to restrict the depth of the insertion of the hollow needles 105, 205, 305 and to provide resistance to unintended shifting and removal of the hollow needles 105, 205, 305. FIGS. 5B and 5C show the hollow needle 305 in place within receiving port 315 with ball bearing spring locks 382 exerting pressure against the hollow needle 305. The pressure exerted by ball bearing spring locks 382 is such that removal of the hollow needle 305 from the receiving port 315 is possible with sufficient axial force applied in a withdrawal direction of the hollow needle 305 relative to the receiving port 315.

Referring to FIGS. 5A-5C, the electrode deployment mechanism is shown. A spring 395 exerts force against the electrode 325 and maintains the electrode 325 in an un-deployed state as shown in FIG. 5A. Once the deployment mechanism is actuated, a top half of a segmented cuff 390 is rotated circumferentially relative to the electrode 325, causing a bottom half of the segmented cuff 390 to exert a downward axial force on the spring 395, causing the spring 395 to compress, forcing the electrode 325 downward through the hollow needle 305. After a first actuation of the deployment mechanism, the electrode 325 is maintained in a deployed state. A second actuation of the deployment mechanism operates to actuate a second rotation of the cuff 390, which decompresses the spring 395. As the spring 395 decompresses, it retracts the electrode 325 into the hollow needle 305. It will be understood that many configurations for deploying and retracting the electrodes are contemplated such as other spring-loaded designs which may include cams, specific electro-mechanical motors or other force-transmitting means suitable for electrode actuation. The mechanism described herein is non-limiting and is intended to describe only one possible embodiment out of many for use in the present invention. One of skill will appreciate that many designs can be used to withdraw, retract and deploy the electrodes without departing from the invention.

Figure 5D:
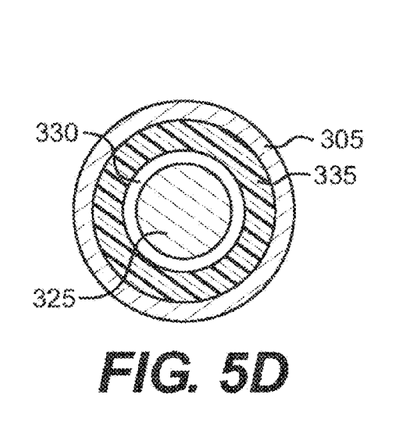
FIGS. 5D and 5E show an end view of cross sections of the hollow needle and electrode shown in FIGS. 5A-5C.
Figure 5E:
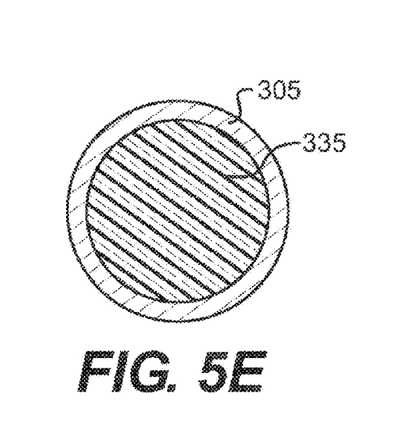

The insulating features of the hollow needle 305 and the configuration of the electrode 325 is illustrated in FIGS. 5D and 5E, which show axial views of the hollow needle 325 at different positions along the length of the needle. FIG. 5D shows a cross section of the hollow needle 305 at a location in the needle in which the electrode 325 is present. FIG. 5E shows a cross section of the hollow needle 305 at the tip of the needle when the electrode 325 is in a non-deployed state and obscured by the sealed tip of the hollow needle 305 filled with the insulating liner 335. In one configuration, the insulating liner 335 and the re-sealable tip are the same material while in another, the insulating liner 335 is a rigid material and is joined with the self sealing material of the re-sealable tip.

Referring to FIGS. 3A-3C, an embodiment of a plug 100 having deployable data electrodes 126 is shown, with the operation of the deployment and retraction of the electrodes 125, 126 depicted. In operation, the plug 100 is inserted into an implantable subcutaneous electrical socket according to the invention through the patient's skin, and force is applied to actuation buttons 102. In one non-limiting embodiment, actuation buttons 102 activate the deployment mechanism described herein and shown in FIGS. 5A-5C, to deploy the electrodes 125, 126. It is understood that any actuation means are contemplated without departing from the invention. The force required to activate the actuation buttons 102 is applied laterally relative to the insertion direction of the plug 100, in order to avoid causing trauma to the patient, and to prevent over-insertion of the electrodes 125, 126 into the implantable subcutaneous electrical socket.

The implantable subcutaneous electrical socket according to the present invention is constructed of a rigid, biocompatible, and electrically insulating material such as silicone, polytetrafluoroethylene, polyethylene tereptphalate, polytetrafluoroethylene, polyurethane, polyvinyl chloride, or any suitable material known to those of skill in the art including materials that comply with ISO 10993. One skilled in the art will recognize that other suitable materials may also be used. The surfaces of the electrical socket can include an antimicrobial treatment and/or material such as silver to reduce the risk of infection that accompanies percutaneous access to a patient. Antimicrobial treatments can include chemical vapor deposition of an antimicrobial substance on the surface of the implantable subcutaneous electrical socket. Antimicrobial materials can include polymers having hydrophobic character and containing an amino group with a pKa greater than or equal to about 8. Antimicrobial treatments and materials can be non-leaching and would not depreciate in efficacy over the life of the implantable socket.

Figures 6A, 6B, 6C:
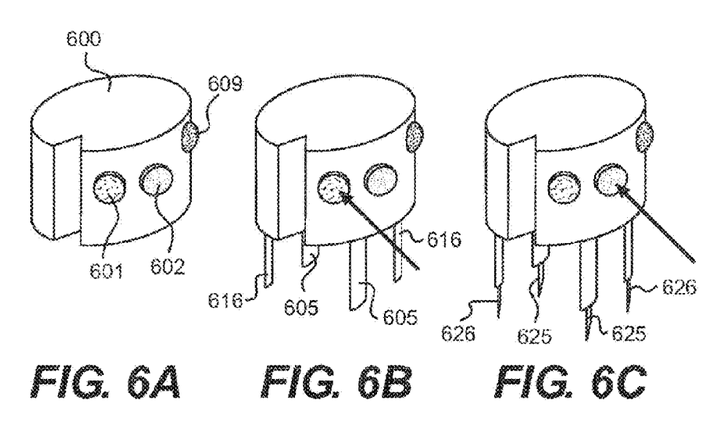
FIGS. 6A-6C show perspective views of an embodiment of a percutaneous plug according to the present invention illustrating actuation of deployable hollow needles and deployable electrodes.

Referring to FIGS. 6A-6C, an embodiment of a plug 600 having deployable hollow needles 605, 616 and deployable electrodes 625, 626 is shown, with the operation of the deployment and retraction of the hollow needles 605, 616 and electrodes 625, 626 depicted. In operation, the plug 600 is aligned with an implanted subcutaneous electrical socket according to the invention, assisted by palpable features of the implanted subcutaneous electrical socket that are complimentary to features of the plug 600 similar to the alignment features of FIG. 1. Once the plug 600 is aligned with the implanted subcutaneous electrical socket, force is applied to actuation buttons 601. Once actuated by actuation buttons 601, hollow needles 605, 616 are deployed from a retracted position within the plug 600, to a percutaneous position wherein upon deployment the hollow needles 605, 616 pierce the skin of the patient as the needles are delivered into corresponding receiving ports of the implanted subcutaneous electrical socket. Once the hollow needles 605, 616 are in place within the receiving ports of the implanted subcutaneous electrical socket, force is applied to actuation buttons 602 to deploy the electrodes 625, 626 independently of the deployment of the hollow needles 605, 616 to establish electrical contact with a conductive base material located at the bottom of the receiving ports. In one non-limiting embodiment, actuation buttons 601, 602 each activate a deployment mechanism similar to that described herein and shown in FIGS. 5A-5C, to deploy the hollow needles 605, 616 and electrodes 625, 626. It is understood that any actuation means are contemplated without departing from the invention. The force required to activate the actuation buttons 601, 602 is applied laterally relative to the insertion direction of the plug 600, in order to avoid causing trauma to the patient, and to prevent over-insertion of the hollow needles 605, 616 and electrodes 625, 626 into the implantable subcutaneous electrical socket (not depicted in FIGS. 6A-C). Diaphragm 609 disposed on plug 600 evacuates air through an airway (not shown) to establish a vacuum seal to inhibit movement of the plug while connected to the implantable subcutaneous electrical socket (not shown).

Figure 7A:
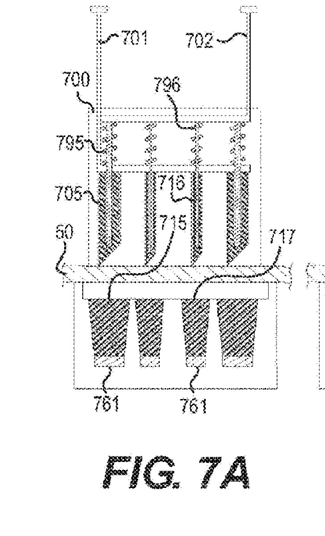
FIGS. 7A-7C show a cut-away side view of an embodiment of a percutaneous plug and implantable subcutaneous electrical socket according to the present invention, and illustrate the deployment of hollow needles into receiving ports followed by deployment of electrodes from the hollow needles.
Figure 7B:
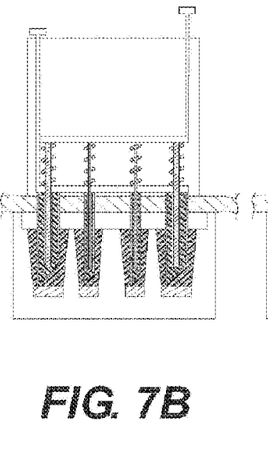
Figure 7C:
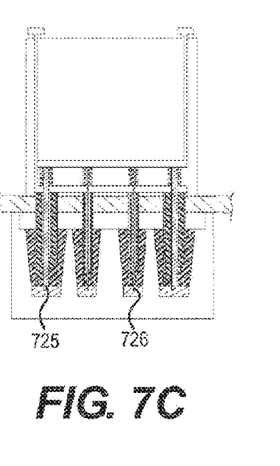

FIGS. 7A-7C, illustrate another embodiment of a deployment mechanism wherein a progression of the deployment of hollow needles 705, 716 and electrodes 725, 726 is shown. As shown, hollow needles 705, 716 are inserted through a patient's skin 50, into receiving ports 715, 717 and electrodes 725, 726 are subsequently deployed into the receiving ports 715, 717 to establish contact with a conductive base material 761. Deployment of the hollow needles 705, 716 is accomplished by exerting force on an actuator 701. Deployment of the electrodes 725, 726 is accomplished by exerting force on an actuator 702. Springs 795, 796 bias the hollow needles 705, 716 and electrodes 725, 726 in an non-deployed position until actuation. In the non-limiting embodiment shown in FIGS. 7A-7C, the actuators 701, 702 are shown axially extending from the plug 700, however other embodiments are contemplated in which the actuators 701, 702 extend circumferentially out of the plug 700 to prevent excessive vertical force from being applied to the plug and socket.

Figure 8A:
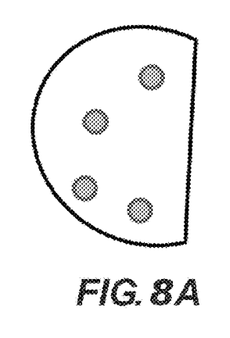
FIGS. 8A-8C are top views showing the shapes of non-limiting embodiments of implantable subcutaneous electrical sockets according to the present invention.
Figure 8B:
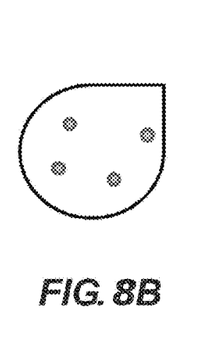
Figure 8C:
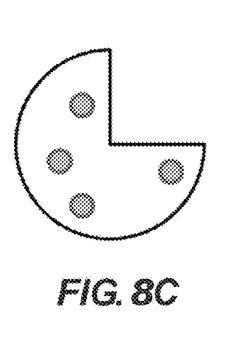

Referring to FIGS. 8A-8C, non-limiting examples of embodiments of implantable subcutaneous electrical sockets having asymmetrical features are shown in top views. The asymmetrical features are selected such that they are palpable through the skin of a patient in order to facilitate alignment of a percutaneous plug with the implanted subcutaneous electrical socket. Additionally, the asymmetric arrangement of receiving ports within the electrical socket restricts connection of a percutaneous plug to ensure that the electrodes of the plug are connected to the correct receiving ports of the implanted subcutaneous electrical socket.

In certain embodiments, the hollow needles have a beveled tip to facilitate piercing the patient's skin. In one embodiment, the tips of the hollow needles have a standard bevel. In another embodiment, the tips of the hollow needles have a short bevel. The hollow needles are constructed of a hard and rigid material that can be suitable for sterilization techniques and suitable for percutaneous insertion. In certain non-limiting embodiments, the hollow needles can range in size from 12 to 34 gauge or 2.77 to 0.18 mm in diameter. In one embodiment, the hollow needles are constructed of surgical stainless steel with an electrically insulating liner of silicone or polyurethane disposed around the inner circumference of the needle, and with a self sealing and electrically insulating silicone material disposed in the tip of the needle. In another embodiment, the hollow needles are constructed of surgical stainless steel and are filled with a self sealing and electrically insulating silicone material. In some embodiments, the surgical stainless steel of the hollow needles is coated by an antimicrobial material, such as silver, to inhibit the introduction of microorganisms into the patient. In other embodiments, the hollow needles are constructed of a polymer, such as polypropylene, polystyrene, polymethylmethacrylate, polycarbonate, or polyvinyl chloride. In some embodiments, the polymer of the hollow needles has antimicrobial properties to inhibit the introduction of microorganisms into the patient.

The electrodes of embodiments of the invention are constructed of a rigid, electrically conducting material, and have a tip that does not damage the sealing materials within the hollow needles. In one embodiment, the electrodes are constructed of surgical stainless steel. In another embodiment, the electrodes are constructed of copper or any suitable electrically conducting material.

The conductive base material of embodiments of the invention may be a rigid or soft material, which may be selected to achieve a certain degree of contact with the electrodes, depending on, for example, the amount of operating current and voltage to be conducted, and/or the magnitude of the data and control signals to be conducted. One skilled in the art will recognize that efficient conductance of high electrical currents and/or voltages require a suitable area of contact between the power electrodes and the conductive base material. The conductive base material may be a powdered material such as metal, graphite, or carbon, or a gelled material. In some embodiments, the conductive base material is penetrable by the electrodes. In other embodiments, the electrodes make a point contact with the conductive base material.

The body of the implantable subcutaneous electrical sockets described herein is sized to accommodate operating currents and voltages suitable for energizing implanted medical devices while minimizing invasiveness to the patient. In one embodiment, the implantable subcutaneous electrical socket is about 25 mm in diameter. The hollow needles and electrodes of the percutaneous plug are sized small enough to minimize patient pain while being sufficiently large to accommodate the operating currents and voltages suitable for energizing an implanted medical device. In certain embodiments, the outer diameter of the hollow needles can range from about 0.3 mm to about 3 mm, with the outer diameter of the electrodes ranging from about 0.1 mm to about 0.6 mm.

One skilled in the art will recognize that the conductivity of a wire depends upon, among other things, the material of construction and the wire diameter. Specifically, the diameter of a wire is largely determinative of the wire's electrical resistance and capacity to carry current. In general, the percent voltage drop along a fixed length of wire for a fixed electrical load decreases as the diameter of the wire increases. Accordingly, one skilled in the art will recognize that various electrode diameters may be suitable for the specific conductivity requirements required for energizing a given implanted medical device.

In one embodiment, the plug and implantable subcutaneous electrical socket are suitable for conducting about 5 to 24 volts of operational voltage from an external power source to an implanted medical device. In other embodiments, the potential can range from about 0.05 to about 20 V. In another embodiment, the plug and implantable subcutaneous electrical socket are suitable for conducting about 0.01 to about 1 amp of operational current from an external power source to an implanted medical device. The power source may supply an alternating current ("AC") or direct current ("DC"). One skilled in the art will recognize that the number, arrangement, and size of the hollow needles and electrodes of the plug may be varied to accommodate various operational currents and voltages and to avoid inducing conductivity of otherwise insulating materials.

In any embodiment the percutaneous plug and implantable subcutaneous electrical socket are suitable for conveying about 0.5 watts of operational power to an implanted medical device. In other embodiments, the percutaneous plug and implantable subcutaneous electrical socket are suitable for conveying about 12 watts of operational power to an implanted medical device. In other embodiments, the plug and implantable subcutaneous electrical socket are suitable for conveying from about 0.1 watts to about 12 watts of operational power.

In any embodiment, the transmission of electricity to an implanted medical device via the implantable subcutaneous electrical socket and percutaneous plug is regulated by an external controller and power source by establishing a closed-loop feedback system between the implanted medical device and the external controller and power source. The operation of the implanted medical device is controlled by an external controller via a closed-loop feedback system between sensors of the implanted medical device and the external controller. The external controller may be programmable to regulate electrical transmission and/or to operate the implanted medical device in a precise fashion selectable by the user.

In embodiments of the implantable subcutaneous electrical socket and percutaneous plug system, electrodes that do not conduct operating current and voltage instead conduct data and control signals between an implanted medical device and an external controller. The data and control signals communicate information about the state and operation of an implanted medical device in order to provide feedback to a physician and/or operator. The implanted medical device can include a hermetically sealed motor. Optionally, the implanted medical device is a bone distraction motor having a rotational encoder that relays the number of turns of the motor. Such encoders are known to those skilled in the art, and can employ an optical sensor and light source for counting the number of revolutions of a motor. As the motor rotates, the encoder turns and intermittently obscures the optical sensor from the light source. The encoder relays the number of instances the light source is obscured to an external controller, and software within the controller translates the data into the number of rotations of the motor and total expansion of the bone distraction device. Motor information is communicated from the implanted medical device, through the implantable subcutaneous electrical socket and percutaneous plug system, and to the external controller, which uses the information and software to regulate the operating current and voltage of the system by controlling a separate or integrated power supply.

In certain embodiments, the implantable subcutaneous electrical socket and percutaneous plug facilitate conveyance of electricity and control signals to an implantable bone distraction motor which operates at low revolutions per minute ("RPM") and delivers a high degree of torque. The bone distraction motor may include a transmission and associated gearing wherein a single rotation or revolution of the motor results in a displacement from about 0.001 to 5 mm in the distraction device to which it is attached.

The nature of the medical device that can be connected to and powered by the electrical socket described herein is not particularly limited. However, in certain embodiments DC motors for use in conjunction with bone distraction are contemplated as benefiting from the ability of the electrical socket to deliver a variable amount of power to an implanted medical device. Many types of DC motors are known in the art including those suitable for implantation in the body.

In certain embodiments, there can be a significant distance between the location of the implanted electrical socket and the motor to be powered. For example, the distraction of long or tubular bones, such as the femur, can be accomplished through use of a intramedullary nail like device that is surgically implanted in the intramedullary space. The intramedullary nail has two movable parts attached to respective bone segments that move in telescopic action either through force applied to a mechanical actuator or hydraulic pump. Along with the intramedullary nail, a DC motor of a size and configuration can be placed in the intramedullary space along with a drive unit and gearing or a transmission to modulate the mechanical output of the DC motor to the expansion components of the intramedullary nail. The intramedullary nail, DC motor and drive unit can be placed in the same housing. Further, a control component that monitors the operation of the DC motor can be included.

The DC motor is connected to the electrical socket through solid conductors that are located within a catheter to prevent any accidental conduction of current to the body of the subject. An opening in the bone to the intramedullary space can be formed during the surgical implantation of the intramedullary nail to allow the solid conductors to connect with the DC motor. The solid conductors can include conductors for carrying electric current to power the DC more and conductors for carrying data information from the control component to the electrical socket.

Prior to implantation, the DC motor and associated gearing or transmission can be calibrated such that the amount of mechanical movement of a distraction device or an intramedullary nail per rotation of the DC motor is known. Using the calibration information, an encoder with optical detector and light source can measure the number of motor rotations. The motor rotation data can be transmitted to a controller located outside the body via the implanted electrical socket. As such, the controller can stop operation of the motor when the DC motor has performed a sufficient number of rotations to achieve the desired adjustment of the distraction device or intramedullary nail.

Measures for control can further include a force sensor that measures the amount of force applied to an actuator or hydraulic pump by the motor, wherein data including force measurements can also be transmitted to the controller via the electrical socket. The amount of electrical power supplied to the motor can be adjusted in response to the force measured by the force sensor. For example, the amount of electrical power supplied to the motor in a manner such that the force applied does not reach a specific threshold. Similarly, an initial supply of electric power can be set at a low value and only increased if a safe amount of force is observed and/or the rate of rotation of the motor is not sufficient.

In certain embodiments, a distraction can be performed on a non-tubular bone such as distraction of the mandible. A distraction apparatus external to the bone can be attached to a bone, such as the mandible, to allow for movement between two bone segments to be controlled. Similar to intramedullary distraction devices, a device for mandibular distraction can contain a DC motor drive unit, gearing or a transmission to modulate the mechanical output of the DC motor to the expansion components of the distraction device, and a control component in a shared housing. The rotation of the DC motor and the force applied by the motor can be monitored by a non-implanted controller in similar fashion as described above.

The motor operating an implanted distraction device can be designed to have a sufficient amount of power to perform a wide range of treatment options. In practice, distraction of a femur generally requires more power than is necessary for distraction of a mandible. Femur distraction adjustments of up to 2 mm are expected to require a maximum of 500-700 Newtons ("N") of force.

By way of example, a distraction of 2 mm requiring 700 N of force would require a total power output (work performed) of 1.4 Joules ("J") of energy. A particularly large femur distraction adjustment of 5 mm with 1500 N of force needed to extend the bone would require 7.5 J. The required power output of the motor required to perform the distraction is dependent upon the duration of the distraction. Assuming a distraction adjustment lasting for a duration of 60 seconds, the necessary power output or wattage would be 7.5 J/60 sec or 0.125 Watts. As such, the electric motor should be able to output at least 0.125 Watts. One skilled in the art will recognize that a significant portion of the power output of any motor will be lost to resistance in the wires and friction in the drive mechanism, and sufficient power should be available to prevent stalling of the device. Therefore, in certain embodiments, the drive mechanism is engineered to have a factor of safety to compensate for frictional losses (factor of 2) and to prevent stalling of the device (factor of 2) where the exemplary motor should have a rating of at least 0.5 Watt, i.e. 0.125 W×2×2. A typical motor envisaged for implantation can operate on a DC current at about 10 to about 18 V, which would require a current of about 0.03 to about 0.05 A. However, those skilled in the art will recognize that any combination of current and voltage potential sufficient to provide the desired power can be used. In certain embodiments, the electric motor can be powered by a current from about 0.01 to about 0.5 A. The electric motor can be operated by a direct current potential from about 0.05 to about 20 V.

In a mandibular distraction scenario, much smaller distractions are typically performed and significantly less force is required to achieve such distractions. A 0.5 mm mandibular extraction might require about 35 N of force, translating to a required energy of 0.0175 J. A distraction of this type performed over the course of 60 seconds would yield a power requirement of 0.0175 J/60 sec or 0.292 mW. Thus a 1 V DC motor could operate at 0.1 A and achieve the necessary power in excess.

Embodiments of implantable subcutaneous electrical sockets according to the present invention are suitable for operation by a medical professional, a patient, or both. In some embodiments, a medical professional in a clinical environment uses a percutaneous plug to connect a control unit and/or power source to an implanted subcutaneous electrical socket to control and/or energize an implanted medical device within a patient according to a treatment regimen selected by the medical professional. In other embodiments, a patient at home similarly uses a percutaneous plug to connect an at-home control unit and/or power source to an implanted subcutaneous electrical socket to control and/or energize an implanted medical device according to a treatment regimen prescribed by a medical professional.

Other objects, features and advantages of the present invention will become apparent to those skilled in the art from the detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

I claim:

1. A medical device, comprising:
   an electrical plug having a skin contact surface and at least two hollow needles, the hollow needles capable of extending from the skin contact surface;
   at least two power electrodes, each power electrode located inside one of the hollow needles to form a hollow needle having a power electrode, said power electrodes connected to an electric power source and movable between a non-deployed position where contacting ends of the electrodes do not protrude from the hollow needles and a deployed position where the contacting ends of the electrodes protrude from the hollow needles; and
   an implantable subcutaneous electrical socket having a plurality of receiving ports configured to receive the hollow needles, each receiving port electrically insulated from each of the plurality of receiving ports and having one or more lateral walls and a base defining a receptor space, where the base has a conductive base material.

2. The medical device of claim 1, wherein the hollow needles are movable between a retracted position where the hollow needles do not extend from the skin contact surface and a percutaneous position where the hollow needles extend from the skin contact surface in a configuration to be received by the receiving ports, wherein each power electrode can be deployed independent of the position of the hollow needles.

3. The medical device of claim 1, wherein the implantable subcutaneous electrical socket is electrically connected to an implantable medical device.

4. The medical device of claim 3, wherein the hollow needles are moveable between a retracted position and a percutaneous position by a spring or cam actuated mechanism.

5. The medical device of claim 1, wherein the electrical plug further comprises an insulating material that insulates the power electrodes from electrical contact with the hollow needles.

6. The medical device of claim 1, where the implantable subcutaneous electrical socket further comprises an insulating material filled in the receptor space of the plurality of receiving ports and between the receiving ports, the insulating material having a composition such that the insulating material is penetrable by the hollow needles and re-sealable upon removal of the hollow needles to insulate the conductive base material in the plurality of receiving ports.

7. The medical device of claim 1, wherein the electrical plug further comprises one or more data electrodes extending from the skin contact surface, the data electrodes having a needle structure to pierce the skin and to be received by one or more of the plurality of receiving ports of the implantable subcutaneous electrical socket, said one or more data electrodes connected to a controller capable of modifying an electrical current supplied by the electric power source to the power electrodes.

8. The medical device of claim 1, wherein the electrical plug further comprises one or more data electrodes extending from the skin contact surface, each of the one or more data electrodes located inside one of the at least two hollow needles to form a hollow needle having a data electrode, said one or more data electrodes movable between a non-deployed position where contacting ends of the data electrodes do not protrude from the hollow needles and a deployed position where the contacting ends of the data electrodes protrude from the hollow needles, said data electrodes connected to a controller capable of modifying an electrical current supplied by the electric power source to the power electrodes.

9. The medical device of claim 8, wherein at least one of the hollow needles has a different diameter than another of the hollow needles, and at least one of the receptor spaces of the plurality of receiving ports has a different diameter than another receptor space of the plurality of receiving ports.

10. The medical device of claim 9, wherein at least one of the hollow needles has a diameter such that the hollow needle cannot enter the receptor space of at least one of the receiving ports.

11. The medical device of claim 10, wherein the plurality of hollow needles and the plurality of receiving ports are arranged such that each hollow needle can only enter a specific receiving port.

12. The medical device of claim 1, wherein at least one of the hollow needles contains a re-sealable insulating material that does not impede movement of the power electrode from the non-deployed to deployed positions.

13. The medical device of claim 12, wherein the insulating material comprises silicone.

14. The medical device of claim 1, wherein at least one of the hollow needles has an interior surface in contact with an insulating material, wherein the insulating material is a material that coats the interior surface.

15. The medical device of claim 1, wherein at least one of the hollow needles has an opening at a piercing end that is sealed with a re-sealable plug pierceable by one of the power electrodes.

16. The medical device of claim 1, wherein at least one of the power electrodes is a needle.

17. The medical device of claim 1, wherein the conductive base material of the receiving ports is a powdered conductive material penetrable by the power electrodes.

18. The medical device of claim 17, wherein the powdered conductive material comprises a metal, an alloy, graphite, a polymer or a gelled material.

19. The medical device of claim 1, wherein the power electrodes do not contact the conductive base material when in the non-deployed position.

20. The medical device of claim 1, wherein the power electrodes contact the conductive base material when in the deployed position such that electrical contact is established between the power electrodes and the conductive base material.

21. The medical device of claim 1, further comprising an electric motor connected to the implantable subcutaneous electrical socket.

22. The medical device of claim 21, wherein the electric motor operates at high torque with low RPM and has associated gearing wherein one rotation of the electric motor and associated gears results in a maximum displacement from about 0.001 mm to 5 mm in a distraction device attached to the implantable electrical socket.

23. The medical device of claim 21, further comprising a control component for modifying an electrical current supplied by the electric power source to the electric motor.

24. The medical device of claim 1, wherein the skin contact surface of the electrical plug has a complementary geometric shape to a subcutaneous surface of the implantable subcutaneous electrical socket to allow for alignment of the plurality of hollow needles with the plurality of receiving ports.

25. The medical device of claim 1, wherein the electrical plug and implantable subcutaneous electrical socket further comprise one or more selected from magnetic components that allow for alignment of the plurality of hollow needles with the plurality of receiving ports, a notched portion on the implantable subcutaneous electrical socket being positionable through the skin to allow for alignment of the plurality of hollow needles with the plurality of receiving ports, and a hollow tube extending from the electrical plug and attached to an external vacuum source to create suction to hold the electrical plug in place on the skin.

26. The medical device of claim 1, further comprising a means for securing the hollow needles within the plurality of receiving ports, wherein the means can regulate an amount of penetration of the hollow needles into the plurality of receiving ports.

27. The medical device of claim 26, wherein the means for securing the hollow needles in the plurality of receiving ports is a ball bearing lock system, wherein a ball structure attached to one of the plurality of receiving ports engages with a groove on one of the power electrodes.

28. The medical device of claim 1, wherein the power electrodes are moveable between the deployed position and the non-deployed position by a spring or cam actuated mechanism.

29. The medical device of claim 1, wherein surfaces of the medical device are formed of an antimicrobial material.

* * * * *